(12) United States Patent
Newsome

(10) Patent No.: US 11,045,568 B2
(45) Date of Patent: Jun. 29, 2021

(54) SAFE SERVE UTENSIL SANITIZING COVER

(71) Applicant: Angela Newsome, Cordova, TN (US)

(72) Inventor: Angela Newsome, Cordova, TN (US)

(*) Notice: Subject to any disclaimer, the term of this patent is extended or adjusted under 35 U.S.C. 154(b) by 0 days.

(21) Appl. No.: 16/583,364

(22) Filed: Sep. 26, 2019

(65) Prior Publication Data

US 2020/0016285 A1 Jan. 16, 2020

Related U.S. Application Data

(60) Provisional application No. 62/770,232, filed on Nov. 21, 2018.

(51) Int. Cl.
*A61L 2/10* (2006.01)
*A61L 2/22* (2006.01)
*A47G 21/02* (2006.01)

(52) U.S. Cl.
CPC ............... *A61L 2/10* (2013.01); *A47G 21/02* (2013.01); *A61L 2/22* (2013.01); *A47G 2400/02* (2013.01); *A61L 2202/11* (2013.01)

(58) Field of Classification Search
USPC .................................................. 250/455.11
See application file for complete search history.

(56) References Cited

U.S. PATENT DOCUMENTS

| | | | |
|---|---|---|---|
| 6,421,921 B1 | 7/2002 | Garneau | |
| 8,058,629 B2 | 11/2011 | Long | |
| 9,376,833 B2* | 6/2016 | Roberts | A61L 2/18 |
| 10,279,061 B2* | 5/2019 | Wyman | A61L 2/18 |
| 10,751,435 B2* | 8/2020 | Wyman | A47K 5/1217 |
| 10,973,605 B2* | 4/2021 | Russ | A61L 2/24 |
| 2002/0112445 A1 | 8/2002 | Scaduto | |
| 2008/0289188 A1 | 11/2008 | Holdbrooks | |
| 2016/0000950 A1 | 1/2016 | Won | |

* cited by examiner

*Primary Examiner* — Phillip A Johnston
(74) *Attorney, Agent, or Firm* — Boudwin Intellectual Property; Daniel Boudwin

(57) ABSTRACT

A safe serve utensil sanitizing cover including a cylindrical body, which has an internal compartment. The internal compartment is configured to accept a utensil handle. The cylindrical body has a germicidal ultraviolet light disposed within. The germicidal ultraviolet light is pointed into the internal compartment. A gel compartment is disposed within the cylindrical body. The gel compartment has an insert opening disposed within the cylindrical body to connect to the charging port for refilling the gel. The gel compartment also has a gel release device connected to the gel compartment. The gel release device will allow gel to be released onto a utensil handle cover. The gel within the gel compartment is a sanitizing gel.

15 Claims, 4 Drawing Sheets

SAFE SERVE UTENSIL SANITIZING COVER

CROSS REFERENCE TO RELATED APPLICATIONS

This application claims the benefit of U.S. Provisional Application No. 62/770,232 filed on Nov. 21, 2018. The above identified patent application is herein incorporated by reference in its entirety to provide continuity of disclosure.

BACKGROUND OF THE INVENTION

The present invention provides safe utensil handle and sanitizing protection cover that continuously sterilizing serving utensils in use.

Many people enjoy eating at social events and restaurants especially buffet style restaurant or outdoor picnics. These sort of eating arrangements require serving utensils. The utensils are handled by every person that wants some of each respective dish. Constant, multiple, use can cause germs to be passed from one person to the next. In this environment, people can become ill soon after eating at such an event due to the spreading of various germs.

Germs can be easily spread from physical contact with the serving utensils. Some germs can live for days on serving utensils. Germs cause illness amongst people. Typically, people do not clean their hands in between each time they get a serving of food to when they begin eating. This can enhance the spread of germs.

Consequently, there is a need for an improvement in the art of serving utensils. The present invention substantially diverges in design elements from the known art, while at the same time solves a problem many people face when attempting to keep serving utensils clean. In this regard, the present invention substantially fulfills this need.

SUMMARY OF THE INVENTION

The present invention provides a safe serve utensil sanitizing cover, wherein the same can be utilized for providing convenience for the user when using a serving utensil. The safe serve utensil sanitizing cover comprises a cylindrical body having a first end and a second end, wherein the body has an interior volume. The cylindrical body has an opening at the first end, wherein the opening leads to an internal chamber. The internal chamber is configured to receive a handle of a service utensil. The cylindrical body has a gel compartment disposed, therein. The gel compartment has an insert opening disposed therein, whereto connect to the charging port to refill the gel. The gel compartment also has a release device coupled thereto, wherein the release device is configured to release the contents of the gel compartment onto the external chamber. The release device is electrically coupled to a button.

Another object of the safe serve utensil sanitizing cover is to have the button is disposed on the exterior of the cylindrical body.

Another object of the safe serve utensil sanitizing cover is to have a germicidal ultraviolet light within the cylindrical body, wherein the germicidal ultraviolet light is directed into the internal chamber.

Another object of the safe serve utensil sanitizing cover is to have a power source located within the cylindrical body.

Another object of the safe serve utensil sanitizing cover is to have a charging port located on the second end of the cylindrical body, wherein the charging port is coupled to the power source.

Another object of the safe serve utensil sanitizing cover is to have a gel reservoir located in the center of the charging port, wherein the sanitizing handle covers can charge and refill gel.

Another object of the safe serve utensil sanitizing cover is to have a window positioned on the cylindrical body that allows a view into the internal chamber.

Another object of the safe serve utensil sanitizing cover is to have a light located on the cylindrical body, wherein the light illuminates when the power source is charged.

Another object of the safe serve utensil sanitizing cover is to have a friction catch located within the internal chamber, wherein the friction catch holds a handle, therein.

Other objects, features and advantages of the present invention will become apparent from the following detailed description taken in conjunction with the accompanying drawings.

BRIEF DESCRIPTION OF THE DRAWINGS

Although the characteristic features of this invention will be particularly pointed out in the claims, the invention itself, and manner in which it may be made and used, may be better understood after a review of the following description, taken in connection with the accompanying drawings, wherein like numeral annotations are provided throughout.

DETAILED DESCRIPTION OF THE INVENTION

Figure 1:
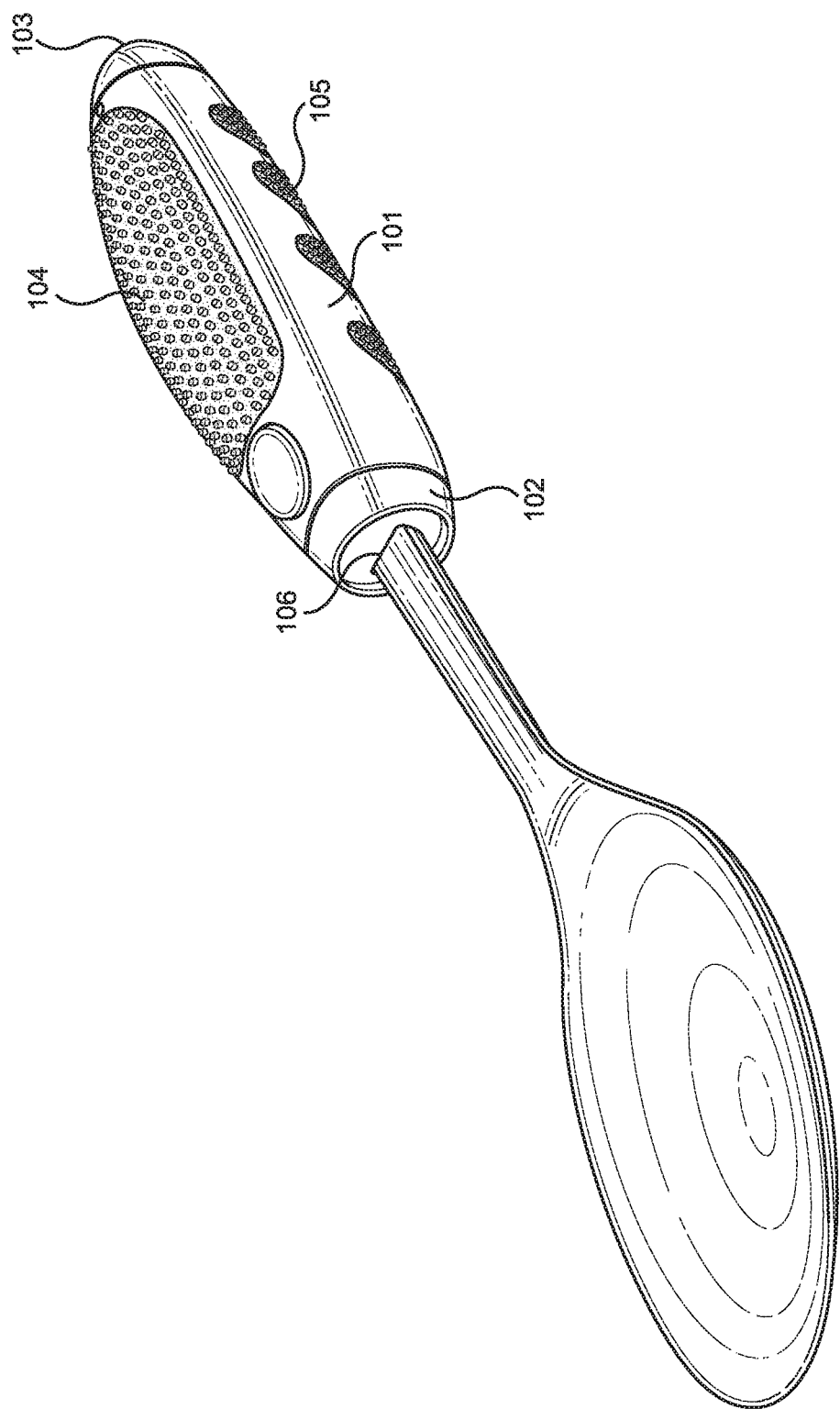
FIG. 1 shows a perspective view of an embodiment of the safe serve utensil sanitizing cover.

Reference is made herein to the attached drawings. Like reference numerals are used throughout the drawings to depict like or similar elements of the safe serve utensil sanitizing cover. For the purposes of presenting a brief and clear description of the present invention, a preferred embodiment will be discussed as used for the safe serve utensil sanitizing cover. The figures are intended for representative purposes only and should not be considered to be limiting in any respect.

Referring now to FIG. 1, there is shown a perspective view of an embodiment of the safe serve utensil sanitizing cover. The safe serve utensil sanitizing cover has a housing 101 having a first end 102 and a second end 103. In one embodiment, the housing 101 is a cylindrical body. In another embodiment, the housing 101 is rectangular body. The housing 101 should have a shape that is easy to grasp and sits comfortably in the hand. In some embodiments, the housing can be thicker in the middle and taper toward the first end 102 and second end 103.

In one embodiment, the housing 101 has a first window 104 located within the housing 101. In one embodiment, the first window 104 will allow a user to be able to see into the housing. In one embodiment, the first window 104 has a textured surface. The textured surface will allow for the housing 101 to be easier to hold. In one embodiment, there is a second window 105 on a side opposite the first window 104. The second window 105 may also have a textured surface.

The housing 101 has an opening 106 at the first end 102. The opening 106 is large enough to fit the handle end of a serving utensil. The opening 106 is connected to an internal compartment. The internal compartment is a long chamber that goes through the housing 101. In one embodiment, the opening 106 is flexible. In this embodiment, the flexible opening 106 can hold the handle end of a service utensil by friction. In another embodiment, the opening 106 is in a fixed position. In this embodiment, there is a friction hold located within the internal compartment.

Figure 2:
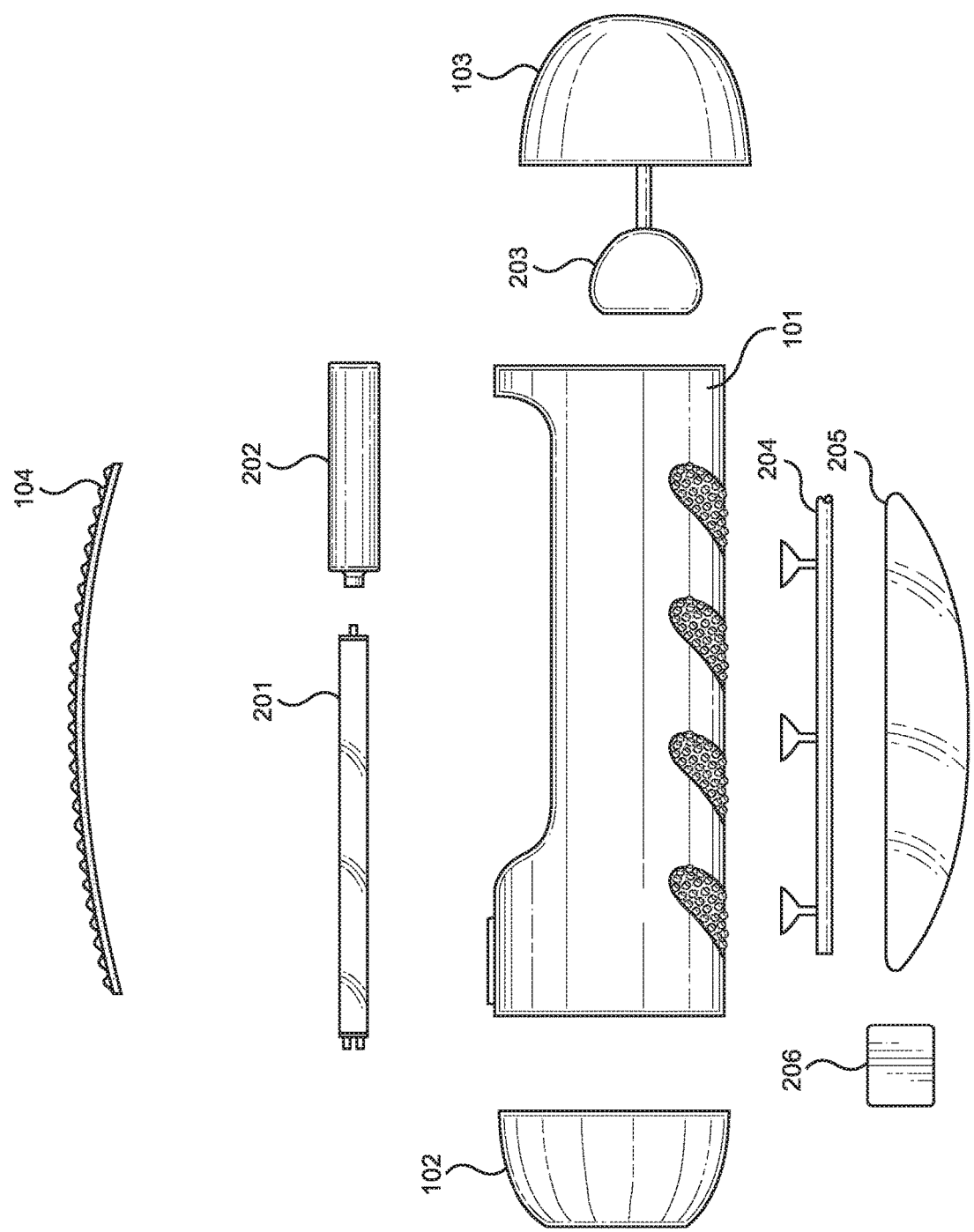
FIG. 2 shows an exploded view of an embodiment of the safe serve utensil sanitizing cover.

Referring now to FIG. 2, there is shown an exploded view of an embodiment of the safe serve utensil sanitizing cover. The inside of the housing 101 having a first end 102 and a second end 103 containing a germicidal ultraviolet light 201. The germicidal ultraviolet light 201 allows for sanitizing of the service utensil handle to take place. The germicidal ultraviolet light can be of varying strengths providing that the strength is sufficient to kill germs and bacteria. The germicidal ultraviolet light is connected to a power source 202. In one embodiment, the power source 202 is a rechargeable battery. In the embodiment, where the power source 202 is a rechargeable source, the power source is coupled to a charging port 203. The charging port is located in the second end 103 of the housing. The charging port 203 is located such that a charger may be inserted into the port. In one embodiment, there is a charging port cover 208 removable secured to the port.

There is a gel compartment 205. The gel compartment 205 is capable of holding a gel or liquid substance. In one embodiment, the gel compartment 205 holds a sanitizing gel. In many embodiments, the gel is a food safe sanitizing gel. In one embodiment, the gel is a sani-T-10 gel. In one embodiment, the gel compartment 205 is a solid compartment. In one embodiment, the gel compartment 205 is a flexible compartment.

The gel compartment 205 is fluidly attached to a gel dispensing device 206. In one embodiment, the gel dispensing device 206 is a pump. In this embodiment, the gel dispensing device is operably coupled to the power supply 202. In another embodiment, the gel dispensing device 206 is activated by squeezing the housing. In this embodiment, the gel dispensing device 206 will squeeze the gel compartment extruding the contents from therein when the housing is squeezed. In an embodiment, the gel dispensing device 206 is fluidly coupled to a hose with a plurality of nozzles attached 204. The hose with the plurality of nozzles 204 will help to disperse the gel onto a service utensil handle cover.

Figure 3:
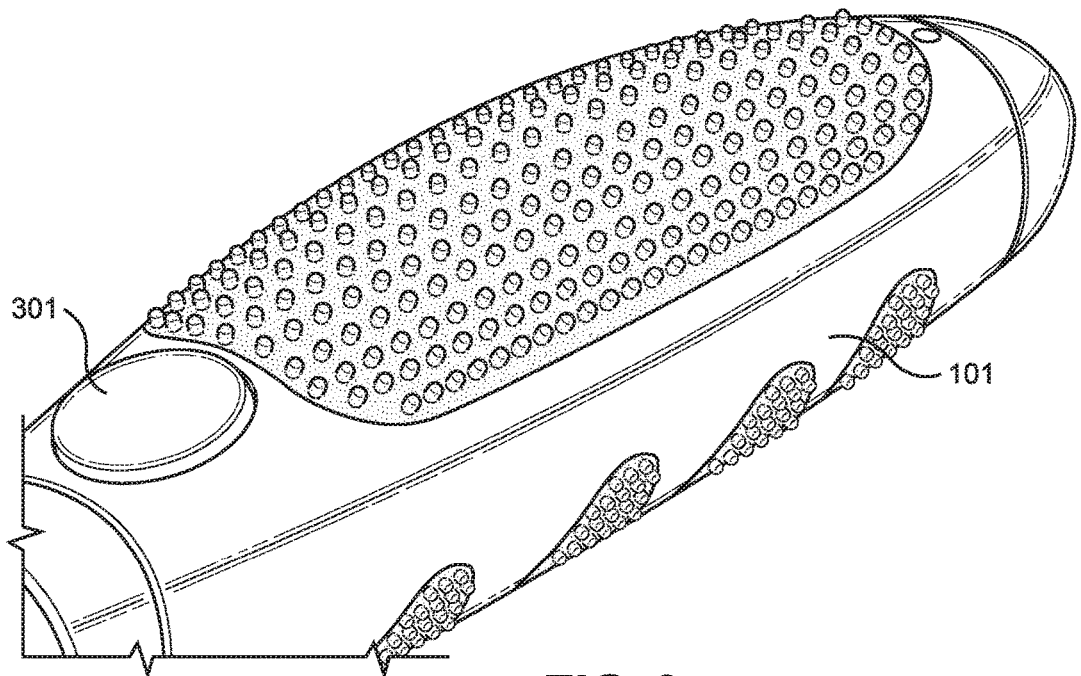
FIG. 3 shows a close-up view of an embodiment of the safe serve utensil sanitizing cover.

Referring now to FIG. 3, there is shown a close-up view of an embodiment of the safe serve utensil sanitizing cover. There is a button 301 located on the housing 101. The button 301 passes through the housing and into the interior of the housing 101. The button 301 is operably coupled to the gel dispensing device. When the button 301 is pressed, the gel dispensing device is activated. In one embodiment, the button 301 will also be operably coupled to the germicidal ultraviolet light. In this embodiment, both the gel disposing device and the germicidal ultraviolet light will be activated upon a press of the button 301.

Figure 4:
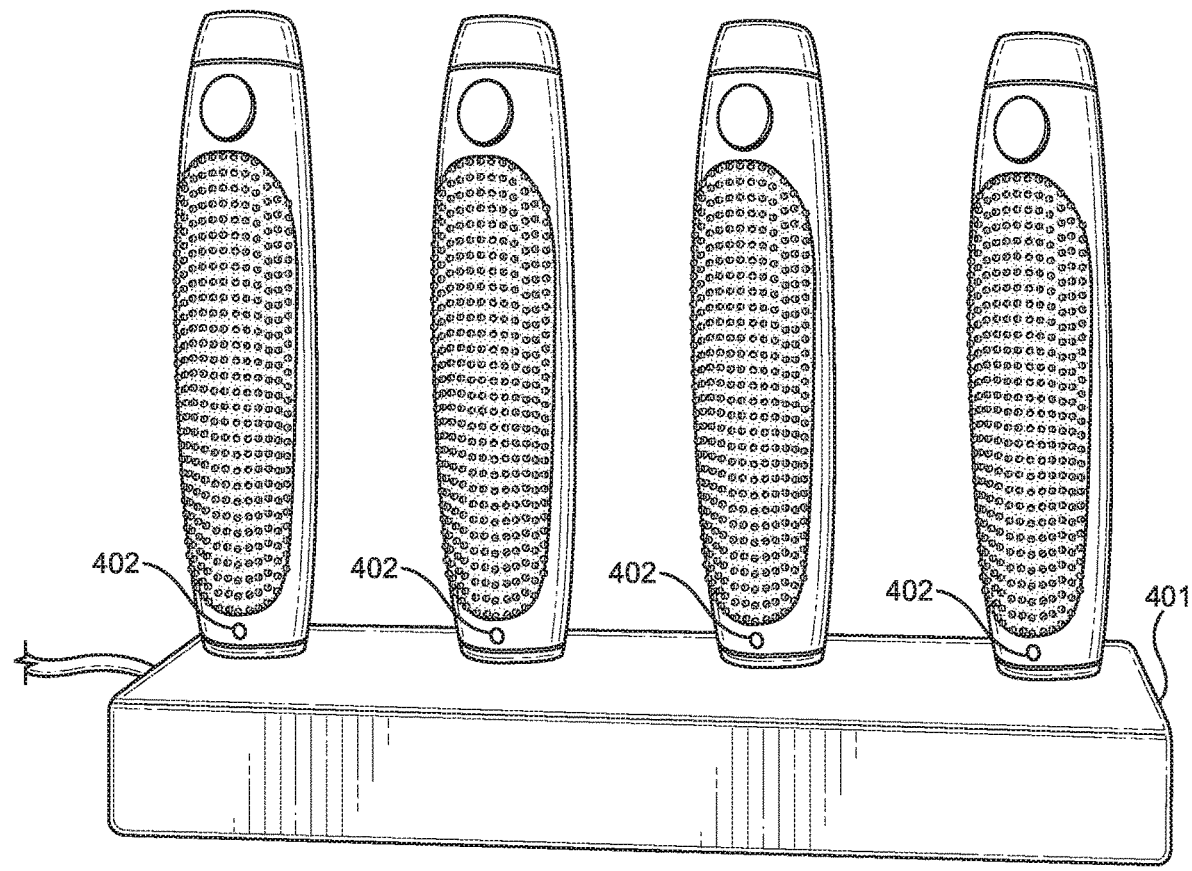
FIG. 4 shows a perspective view of an embodiment of a plurality of safe serve utensil sanitizing covers on a charging base.

Referring now to FIG. 4, there is shown a perspective view an embodiment of a plurality of safe serve utensil sanitizing covers on a charging base. In one embodiment, the power source is a rechargeable battery. In one embodiment, the charging port is configured to be connected to a charging source via a charging base 401. The charging base 401 is designed to allow the safe serve utensil sanitizing cover to be placed therein and remain attached until removed. In one embodiment, there is a light 402 disposed on the housing. The light 402 will illuminate when the safe serve utensil sanitizing cover is attached to the charging platform 401. In one embodiment, the illumination will light red when the power supply is charging and will illuminate green when the power supply is charged completely.

Figure 5:
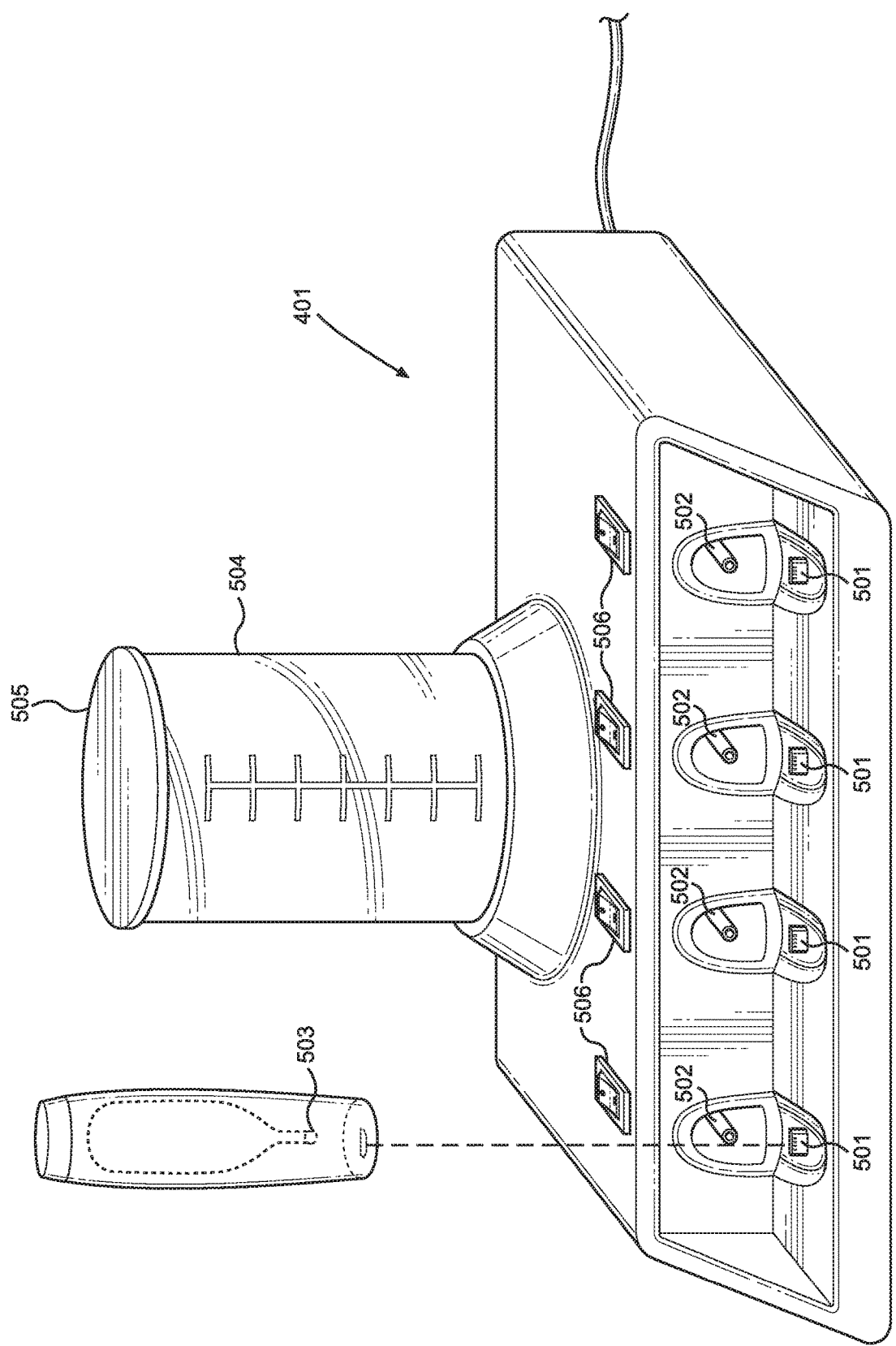
FIG. 5 shows a perspective view of a different embodiment of the charging base for the safe serve utensil sanitizing covers.

Referring now to FIG. 5, there is shown a perspective view of a different embodiment of the charging base for the safe serve utensil sanitizing covers. In this embodiment of the charging base 401 there is an electric charging port 501 and a refilling port 502. The charging port 501 and the refilling port 502 are located within the charging base 401. The two ports are located in the base of the charging base. The two ports are located such that each will be able to connect to the safe serve utensil sanitizing cover at the same time. In one embodiment the back side of the safe serve utensil sanitizing cover has a refill entrance port 503 that is fluidly connected to a gel reservoir 504.

The charging base 401 is adapted to have a gel reservoir 504. The gel reservoir 504 is refillable and is connected to the charging base 401. In one embodiment the gel reservoir 504 has a lid 505 attached to the topside thereof. The gel reservoir 504 has an electric pump located within the housing of the charging base. The pump is configured to remove gel from the gel reservoir when activated and into the safe serve utensil sanitizing cover. The gel reservoir 504 is fluidly connected to the refilling port 502. In one embodiment there will be an on/off switch 506 connected to each refilling port 502. This will allow a user to determine which refilling port will allow gel to be pushed therethrough.

It is therefore submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A safe serve utensil sanitizing cover, comprising:
a housing comprising a first end and a second end;
the first end having an opening that provides access to a recessed section within the housing;
the recessed section configured to removably secure a handle of a utensil therein, such that a portion of the handle extends outwardly through the opening;
a germicidal ultraviolet light disposed within the housing;
a sanitizing gel compartment disposed within the housing, the sanitizing gel compartment having one or more gel dispensing nozzles operably connected to a gel dispensing device, wherein the one or more gel dispensing nozzles are configured to dispense a sanitizing gel material stored within the sanitizing gel compartment onto the utensil handle when the gel dispensing device is activated.

2. The safe serve utensil sanitizing cover of claim 1, wherein the handle of the utensil is removably secured within the recessed section via friction fit.

3. The safe serve utensil sanitizing cover of claim 1, wherein the dispensing device is integral with the gel compartment, such that squeezing the gel compartment causes material to be released from the gel compartment through the one or more gel dispensing nozzles.

4. The safe serve utensil sanitizing cover of claim 1, wherein the dispensing device is a pump operably connected to a control button disposed on an exterior of the housing, such that activating the control button causes the pump to activate to dispense material.

5. The safe serve utensil sanitizing cover of claim 1, wherein the germicidal ultraviolet light is operably connected to a control button disposed on an exterior of the housing, such that activating the control button causes the germicidal ultraviolet light to illuminate.

6. The safe serve utensil sanitizing cover of claim 1, wherein the housing is cylindrical.

7. The safe serve utensil sanitizing cover of claim 1, wherein the housing includes opposing tapered ends, such that the first end and the second end include a width that is less than a width of a central area of the housing.

8. The safe serve utensil sanitizing cover of claim 1, wherein the germicidal ultraviolet light is directed into the recessed section of the housing.

9. The safe serve utensil sanitizing cover of claim 1, further comprising a power source located within the housing and operably connected to the germicidal ultraviolet light.

10. The safe serve utensil sanitizing cover of claim 4, wherein the pump is also operably connected to the power source.

11. The safe serve utensil sanitizing cover of claim 10, further comprising a charging port located on the second end of the cylindrical body, wherein the charging port is coupled to the power source.

12. The safe serve utensil sanitizing cover of claim 11, further comprising a charging indicator light located on the housing, wherein the light is configured to illuminate when the power source is charged.

13. The safe serve utensil sanitizing cover of claim 11, further comprising a charging base having an operably connected gel reservoir, wherein the charging base is configured to charge the power source via a connection to the housing charging port, and wherein gel reservoir is configured to transport material to the housing when the housing is connected to the charging base and a control on the charging base is activated.

14. The safe serve utensil sanitizing cover of claim 1, further comprising a window positioned on the housing that makes visible the recessed section of the housing.

15. The safe serve utensil sanitizing cover of claim 14, wherein the window comprises a plurality of projections defining a textured surface that improves user grip.

* * * * *